United States Patent
Chandrashekhar et al.

(10) Patent No.: US 11,364,196 B2
(45) Date of Patent: *Jun. 21, 2022

(54) LEVOTHYROXINE FORMULATIONS FOR ORAL USE

(71) Applicant: LEIUTIS PHARMACEUTICALS PVT. LTD., Hyderabad (IN)

(72) Inventors: Kocherlakota Chandrashekhar, Secunderabad (IN); Banda Nagaraju, Hyderabad (IN)

(73) Assignee: LEIUTIS PHARMACEUTICALS PVT. LTD., Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/773,619

(22) PCT Filed: Nov. 3, 2016

(86) PCT No.: PCT/IB2016/056615
§ 371 (c)(1),
(2) Date: May 4, 2018

(87) PCT Pub. No.: WO2017/077476
PCT Pub. Date: May 11, 2017

(65) Prior Publication Data
US 2019/0060217 A1 Feb. 28, 2019

(30) Foreign Application Priority Data
Nov. 4, 2015 (IN) .......................... 5957/CHE/2015

(51) Int. Cl.
*A61K 31/198* (2006.01)
*A61K 47/40* (2006.01)
*A61K 9/00* (2006.01)
*A61K 47/10* (2017.01)
*A61K 47/18* (2017.01)

(52) U.S. Cl.
CPC ............ *A61K 9/006* (2013.01); *A61K 31/198* (2013.01); *A61K 47/10* (2013.01); *A61K 47/183* (2013.01); *A61K 47/40* (2013.01)

(58) Field of Classification Search
CPC ...................................................... A61K 9/006
See application file for complete search history.

(56) References Cited

U.S. PATENT DOCUMENTS

| | | | |
|---|---|---|---|
| 2,889,363 A | 6/1959 | Ginger et al. | |
| 2,889,364 A | 6/1959 | Ginger et al. | |
| 5,955,105 A | 9/1999 | Amit et al. | |
| 6,056,975 A | 5/2000 | Amit et al. | |
| 9,006,289 B2 | 4/2015 | Jiang et al. | |
| 2006/0194762 A1* | 8/2006 | Reer | A61K 31/724 514/58 |
| 2009/0105314 A1* | 4/2009 | Ii | A61K 31/215 514/359 |
| 2014/0073695 A1 | 3/2014 | Psarrakis et al. | |

FOREIGN PATENT DOCUMENTS

WO 2007077252 A1 7/2007

OTHER PUBLICATIONS

International Search Report and Written Opinion for PCT/IB2016/056615, dated Jan. 13, 2017.

* cited by examiner

*Primary Examiner* — Yong S. Chong
(74) *Attorney, Agent, or Firm* — Heslin Rothenberg Farley & Mesiti P.C.

(57) ABSTRACT

The present invention relates to novel oral spray formulations of Levothyroxine. Further the invention also describes process for preparing such formulations.

6 Claims, No Drawings

LEVOTHYROXINE FORMULATIONS FOR ORAL USE

CROSS REFERENCE TO RELATED APPLICATIONS

This application is a U.S. National Phase filing under 35 U.S.C. § 371 of International Application PCT/IB2016/056615, filed Nov. 3, 2016, and published as WO 2017/077476 A1 on May 11, 2017. PCT/IB2016/056615 claims priority from Indian Patent Application Number 5957/CHE/2015, filed Nov. 4, 2015. The entire contents of each of these applications are hereby incorporated herein by reference.

BACKGROUND OF THE INVENTION

Thyroxine active drugs are known for both therapeutic and prophylactic treatment of thyroid disorders. The thyroid accomplishes its regulation functions by producing the hormones L-triiodothyronine (liothyronine; T3) and L-thyroxine (levothyroxine; T4). The physiological actions of thyroid hormones are produced predominantly by T3, the majority of which (approximately 80%) is derived from T4 by deiodination in peripheral tissues.

Administration of levothyroxine sodium provides T4 to a patient. Once absorbed in the body, the administered T4 behaves identically to T4 that otherwise would be secreted by the thyroid gland of the patient. It binds to the same serum proteins, providing a supply of circulating T4-thyroglobulin in the patient. The administered T4 may be deiodinated in vivo to T3. As a result, a patient receiving appropriate doses of levothyroxine sodium will exhibit normal blood levels of T3, even when the patient's thyroid gland has been removed or is not functioning.

Levothyroxine sodium is prescribed for thyroid hormone replacement therapy in cases of reduced or absent thyroid function in e.g., ailments such as myxedema, cretinism and obesity. Levothyroxine sodium is quite unstable, hygroscopic and degrades rapidly when subjected to high humidity, light or high temperature. Because of the physicochemical properties of the drug, formulations of levothyroxine sodium have extremely short shelf life.

Levothyroxine sodium is available in the form of capsules, tablets and injection. The injection formulation is available as sterile lyophilized product for parenteral administration containing 100 mcg/vial, 200 mcg/vial and 500 mcg/vial.

U.S. Pat. Nos. 2,889,363 and 2,889,364 to Ginger et al., disclose processes for producing thyroxine sodium.

U.S. Pat. Nos. 5,955,105 and 6,056,975 to Amit et al., disclose solid pharmaceutical preparation of thyroxine drug.

U.S. Pat. No. 9,006,289 to Jiang et al., discloses lyophilized composition comprising of levothyroxine sodium, phosphate buffer and mannitol.

U.S. application 20140073695 to Yannis et al., discloses a method for the preparation of an oral levothyroxine composition.

The oral formulations cannot deliver the drug into the blood at a rapid rate like the injections. On the other hand the injection formulations are associated with painful administration to the patient. The present inventors have developed stable oral spray formulations of Levothyroxine that help in overcoming the disadvantages associated with the prior art formulations. These formulations may provide substantial benefits compared to oral and other modes of drug administration, such as faster appearance of the pharmaceutically active ingredient in the blood, improved dosage reliability, improved safety profile, increased bioavailability and improved patient compliance. Moreover the manufacturing process time is reduced and does not require any specialized equipment unlike the commercially available formulations, thus making it cost efficient process.

SUMMARY OF THE INVENTION

One object of the invention provides stable oral spray formulations of Levothyroxine and methods of preparing such formulations.

Another aspect of the invention is to provide stable oral spray formulations comprising Levothyroxine sodium, buffering agents or pH adjusting agents, one or more solvents and other pharmaceutically acceptable excipients.

DETAILED DESCRIPTION OF THE INVENTION

The present invention relates to a stable oral spray formulation of Levothyroxine. More particularly the invention relates to a stabilized Levothyroxine spray formulation comprising buffering agents, solvents, and other pharmaceutically acceptable excipients.

In the context of this invention "Levothyroxine" refers to pharmaceutically acceptable salts, solvates, hydrates and anhydrous forms thereof. The formulations of the present invention preferably comprise Levothyroxine sodium.

As used herein, "oral spray formulation of Levothyroxine" refers to formulation that contains Levothyroxine in dissolved or solubilized form and is intended for oral administration. The Levothyroxine oral spray formulation may be a clear solution designed to be sprayed directly into the mouth, over or under the tongue.

Levothyroxine sodium is quite unstable, hygroscopic and degrades rapidly when subjected to high humidity, light or high temperature. Degradation is further enhanced by the presence of water. The inventors of the present invention have successfully developed a stable oral liquid spray formulation of Levothyroxine despite its rapid degrading nature.

One embodiment of the invention relates to an oral spray formulation of Levothyroxine comprising Levothyroxine sodium and pharmaceutically acceptable excipients.

Another embodiment of the invention relates to oral spray formulation of Levothyroxine comprising:
i. Levothyroxine
ii. Buffering agents or pH adjusting agents
iii. One or more solvents
and other pharmaceutically acceptable excipients.

Yet, another embodiment of the invention relates to oral spray formulation of Levothyroxine comprising:
i. Levothyroxine
ii. Buffering agents or pH adjusting agents
iii. One or more solvents
iv. Cyclodextrin
and other pharmaceutically acceptable excipients.

A preferred embodiment of the invention relates to oral spray formulation of Levothyroxine comprising:
i. Levothyroxine sodium,
ii. Buffering agents or pH adjusting agents
iii. One or more solvents selected from the group comprising of, water, polyethylene glycol, ethanol, propylene glycol and glycerol
and other pharmaceutically acceptable excipients including cyclodextrin, sweetening agents, flavoring agents, preservatives, penetration enhancers and stabilizers.

In a most preferred embodiment, the oral spray formulation of the present invention comprises:

| | | |
|---|---|---|
| i. | Levothyroxine sodium | 0.0025-5% |
| ii. | Buffering agent or pH adjusting agents | 0.0015-5% |
| iii. | Solvents | qs |
| iv. | Optionally other pharmaceutically acceptable excipients including cyclodextrin, sweetening agents, flavoring agents, preservatives, penetration enhancers and stabilizers. | |

Suitable buffering agents include, but not limited to phosphate, citrate, aconitic, sodium carbonate, sodium bicarbonate, tartarate, benzoate, acetate, boric acid, lactic acid, glutaric acid, malic acid, succinic acid and carbonic acid, alkali or alkaline earth salt of one of these acids, Tris, meglumine, amino acid buffers such as arginine, alanine, histidine, glycine, lysine and the like.

Suitable solvents include, but are not limited to dimethylacetamide (DMA), dimethyl sulfoxide (DMSO), N-Methylpyrrolidone, dimethylisosorbide, ethanol, propylene glycol, polyethylene alcohol, glycerol, propylene glycol esters, polyethylene glycols (PEG) and water. Preferred solvents are water and propylene glycol.

Suitable pH adjusting agents include the following, but are not limited to sodium hydroxide, potassium hydroxide, ammonium carbonate, hydrochloric acid, citric acid, lactic acid, phosphoric acid and sulfuric acid. Preferred pH adjusting agents are sodium hydroxide and hydrochloric acid.

Suitable cyclodextrins include the following, but not limited to α, β and γ-cyclodextrin and cyclodextrins modified with alkyl-, hydroxy alkyl-, dialkyl-, and sulfoalkylether such as methyl or hydroxypropyl β-cyclodextrins (HPCD), methyl-and-ethyl-β-cyclodextrin, sulfoalkylether-substituted beta-cyclodextrin, sulfobutylether-β-cyclodextrin (SBECD) and the like. Substituted beta.cyclodextrins include those substituted with one or more hydrophilic groups, such as monosaccharide (e.g., glucosyl), carboxyalkyl (e.g.,carboxymethyl, carboxyethyl), hydroxyalkyl-substituted (e.g., hydroxyethyl, 2-hydroxypropyl) and the like. Preferably sulfobutylether-β-cyclodextrin (SBECD) is used.

The pharmaceutical formulations of the present invention may also contain one or more anti-oxidants and preservatives such as, but are not limited to butylated hydroxyanisole, butylated hydroxyl toluene, citric acid, lactic acid, benzoic acid, tocopherol, monothioglycerol, ascorbic acid, L-cysteine, methyl paraben, propyl paraben, benzyl alcohol, propyl gallate, thioglycolic acid, citric acid, tartaric acid, phosphoric acid, gluconic acid, thiodipropionic acid, acetonic dicarboxylic acid, sorbic acid and its salts, chelating agents and the like.

The formulation may additionally contain one or more of flavoring or taste-masking agents and sweetening agents. Examples of taste-masking or flavoring agents include, but are not limited to, synthetic or natural peppermint oil, spearmint oil, citrus oil, fruit flavors (e.g., citrus, orange, lemon, strawberry, melon and mixtures) and sweeteners (e.g., sugars, sorbitol, mannitol, dextrose, sucrose, fructose, levulose, aspartame, sodium cyclamate, saccharin, and sucralose).

The formulation may also contain absorption enhancers or penetration enhancers such as, but not limited to surfactants such as sodium lauryl sulfate, sodium dodecyl sulfate, dioctyl sodium sulfosuccinate, tweens, polysorbates, cetylpyridinium chloride, chitosan, trimethyl chitosan, poly-L-arginine and L-lysine; fatty acids and derivatives; bile salts, chelating agents, sulfoxides such as dimethyl sulfoxide (DMSO), decylmethyl sulfoxide; polyols and alcohols.

Optionally stabilizing agents, solubility enhancers and viscosity modifying agents may also be added.

The oral spray formulation can be packed into any suitable containers. Preferred containers are pharmaceutically acceptable glass, polyethyleneterephthalate (PET), high density polyethylene (HDPE), crystal zenith (CZ), polyolefins like polypropylene (PP) or polyethylene (PE), cyclic olefins polymer (COP), cyclic olefin copolymer (COC) bottles, pfeiffer pumps or within any type of pharmaceutically acceptable package, container, pump or bottle.

Comparative dissolution study was performed with Levothyroxine sodium formulation prepared according to the invention and commercially available Levothyroxine sodium tablets (AEB1997, Thyronorm 150 mcg). Dissolution study was performed in 500 ml of 0.01N HCl+0.2% SLS (sodium lauryl sulphate) dissolution media at 50 RPM. Comparative dissolution profiles were recorded and tabulated in table 1.

TABLE 1

| Comparative dissolution profile | | |
|---|---|---|
| Product | Reference product | Invention formulation |
| Strength | 150 mcg (Tablet) | 250 mcg (Oral solution) |
| | % Dissolution | |
| 45 Min | 67 | 95 |

The following examples further describe certain specific aspects and embodiments of the present invention and demonstrate the practice and advantages thereof. It is to be understood that the examples are given by way of illustration only and are not intended to limit the scope of the invention in any manner.

EXAMPLES

Example 1

| S.No | Ingredients | Quantity |
|---|---|---|
| 1 | Levothyroxine sodium | 0.01-1 mg |
| 2 | Arginine | 0.01-4 mg |
| 3 | Propylene glycol | 0.01-1 ml |
| 4 | Sodium hydroxide | q. s |
| 5 | Ultrapure water | q.s to 0.1-2 ml |

Manufacturing Process

Ultrapure water was taken in a compounding vessel and arginine was added and stirred. Propylene glycol was added to the solution and stirred. pH of the solution was adjusted to 11±0.5 by the addition of sodium hydroxide solution. Then the bulk solution was cooled to 2° C. to 8° C. Levothyroxine sodium was added and stirred till a clear solution was obtained, while maintaining the temperature at 5±3° C. The solution was filtered, followed by filling into suitable containers.

Example 2

| S.No | Ingredients | Quantity |
|---|---|---|
| 1 | Levothyroxine sodium | 0.01-1 mg |
| 2 | Alanine | 0.006-4 mg |
| 3 | Propylene glycol | 0.01-1 ml |
| 4 | Sodium hydroxide | q. s |
| 5 | Ultrapure water | q.s to 0.1-2 ml |

Manufacturing Process

Ultrapure water was taken in a compounding vessel and alanine was added and stirred. Propylene glycol was added to the solution and stirred. pH of the solution was adjusted to 11±0.5 by the addition of sodium hydroxide solution. Then the bulk solution was cooled to 2° C. to 8° C. Levothyroxine sodium was added and stirred till a clear solution was obtained, while maintaining the temperature at 5±3° C. The solution was filtered, followed by filling into suitable containers.

Example 3

| | | Quantities in mg | | | |
|---|---|---|---|---|---|
| S.No | Ingredients | F1 | F2 | F3 | F4 |
| 1 | Levothyroxine sodium | 0.5 | 0.5 | 0.5 | 0.5 |
| 2 | Mannitol | 3 | — | — | — |
| 3 | Dibasic sodium phosphate heptahydrate | 0.5 | — | — | — |
| 4 | Arginine | — | 15 | — | — |
| 5 | Alanine | — | — | 6 | — |
| 6 | Glycine | — | — | — | 15 |
| 7 | Sodium hydroxide | q.s to adjust the pH 11.0 ± 1.0 | | | |
| 8 | Ultrapure water | q.s to 1 ml | | | |

Manufacturing Process

Ultrapure water was taken in a compounding vessel and buffering agent (as mentioned in example 3) was added and stirred. Mannitol was added if necessary (F1). pH of the solution was adjusted to 11±1.0 by the addition of sodium hydroxide solution. Then the bulk solution was cooled to 2° C. to 8° C. Levothyroxine sodium was added and stirred till a clear solution was obtained, while maintaining the temperature at 5±3° C. The solution was filtered, followed by filling into suitable containers.

Levothyroxine formulations prepared according to example 3, were tested for stability at 25±2° C./60±5% RH (1 week); 40±2° C./75±5% RH (1 week) and 60±2° C. (3 days). The data is summarized in table 2.

TABLE 2

Stability of the formulation

| Stability Data | F1 | F2 | F3 | F4 |
|---|---|---|---|---|
| Assay | | | | |
| 25 ± 2° C./60 ± 5% RH (1 wk) | 98.1 | 100.5 | 98.4 | 94.5 |
| 40 ± 2° C./75 ± 5% RH (1 wk) | 95.6 | 100.5 | 98.6 | 93.4 |
| 60 ± 2° C. (3 days) | 89.8 | 99.5 | 87.3 | 90 |
| Total Impurities | | | | |
| 25 ± 2° C./60 ± 5% RH (1 wk) | 1.06 | 0.25 | 0.42 | 0.44 |
| 40 ± 2° C./75 ± 5% RH (1 wk) | 1.73 | 0.39 | 0.34 | 0.63 |
| 60 ± 2° C. (3 days) | 4.75 | 1.06 | 1.43 | 3.45 |

Example 4

| S.No | Ingredients | Quantity per mL |
|---|---|---|
| 1 | Levothyroxine sodium | 0.01-1 mg |
| 2 | L-Arginine | 0.01-4 mg |
| 3 | Propylene glycol | 0.02 mL-0.4 mL |
| 4 | Methyl paraben | 0.5-1.5 mg |
| 5 | Sodium hydroxide | q.s |
| 6 | Ultrapure water | qs to 0.1-2 ml |

Manufacturing Process

Ultrapure water was taken in a compounding vessel and L-Arginine was added and stirred. Propylene glycol was added to the solution and stirred. Methyl paraben was added. pH of the solution was adjusted to 11±0.5 by the addition of sodium hydroxide solution. The solution was cooled to 2° C. to 8° C. Levothyroxine sodium was added and stirred till a clear solution was obtained. The solution was filtered, followed by filling into suitable containers.

Example 5

| S.No | Ingredients | Quantity per mL |
|---|---|---|
| 1 | Levothyroxine sodium | 0.01-1 mg |
| 2 | L-Arginine | 0.01-4 mg |
| 3 | Propylene glycol | 0.02 mL-0.4 mL |
| 4 | Propyl paraben | 0.05-0.5 mg |
| 5 | Sorbitol | 0.5-1.5 mg |
| 6 | Sodium hydroxide | q.s |
| 7 | Ultrapure water | q.s to 1.0 mL |

Manufacturing Process

Ultrapure water was taken in a compounding vessel and L-Arginine was added and stirred. Propylene glycol was added to the solution and stirred. Propyl paraben was added. Sorbitol was added to the solution and stirred. pH of the solution was adjusted to 11±0.5 by the addition of sodium hydroxide solution. The solution was cooled to 2° C. to 8° C. Levothyroxine sodium was added and stirred till a clear solution was obtained. The solution was filtered, followed by filling into suitable containers.

Example 6

| S.No | Ingredients | Quantity per mL (A1) | Quantity per mL (A2) |
|---|---|---|---|
| 1 | Levothyroxine sodium | 0.01-2 mg | 0.01-2 mg |
| 2 | Arginine | 0.01-4 mg | 0.01-4 mg |
| 3 | SBECD | 100-400 | 100-400 |
| 4 | Potassium sorbate | — | 2-6 mg |
| 5 | Sodium iodide | 0.5-4.0 | 0.5-4.0 |
| 6 | Ultrapure water | q.s to 1.0 mL | q.s to 1.0 mL |

Manufacturing Process

Ultrapure water was taken in a compounding vessel and SBECD, levothyroxine, Arginine, potassium sorbate and sodium iodide were added and stirred. pH of the solution was adjusted to 6±0.5 with sodium hydroxide or hydrochloric acid. The solution was filtered, followed by filling into suitable containers.

Levothyroxine formulations prepared according to example 6, were tested for stability at 2-8° C., 25±2°

C./60±5% RH and 40±2° C./75±5% RH for a period of 3 months. The data is summarized in table 3.

TABLE 3

Stability of the formulation

| Stability data | A1 | | A2 | |
|---|---|---|---|---|
| Stability duration | 1M | 3M | 1M | 3M |
| Assay | | | | |
| 2-8° C. | 98.3 | 97.3 | 100.9 | 100.3 |
| 25 ± 2° C./60 ± 5% RH | 98.3 | 97.2 | 98.9 | 100.1 |
| 40 ± 2° C./75 ± 5% RH | 97.9 | 97.1 | 100.5 | 99.8 |
| Total Impurities | | | | |
| 2-8° C. | 0.62 | 0.88 | 0.66 | 0.95 |
| 25 ± 2° C./60 ± 5% RH | 0.62 | 0.92 | 0.73 | 0.95 |
| 40 ± 2° C./75 ± 5% RH | 0.72 | 1.16 | 0.87 | 1.29 |

We claim:

1. A spray formulation of Levothyroxine comprising:
   (i) levothyroxine sodium in a concentration of 0.0025-5% by weight of the total formulation;
   (ii) buffering agents or pH adjusting agents selected from arginine or alanine in a concentration of 0.0015-0.5% by weight of the total formulation;
   (iii) one or more solvents, wherein the solvents are selected from one or more of propylene glycol, glycerol, polyethylene glycol (PEG), and water;
   (iv) sulfobutylether-β-cyclodextrin (SBECD); and
   (v) one or more pharmaceutically acceptable excipients, wherein the pH of the formulation is between 5.5 and 6.5.

2. A spray formulation of Levothyroxine according to claim 1 further comprising buffering agents selected from phosphate, citrate, sodium carbonate, sodium bicarbonate, tartarate, benzoate, lactate, acetate, glutaric, malic, succinic acid, carbonic acid, Tris, and meglumine.

3. A spray formulation of Levothyroxine according to claim 1 further comprising sodium hydroxide, potassium hydroxide, ammonium carbonate, hydrochloric acid, citric acid, lactic acid, phosphoric acid, or sulfuric acid.

4. The spray formulation of claim 1, wherein the pharmaceutically acceptable excipients are selected from sweetening agents, flavoring agents, preservatives, penetration enhancers and stabilizers.

5. The formulation of claim 1, wherein the concentration of SBECD ranges from 10-40% by weight of the total formulation.

6. A spray formulation of levothyroxine comprising:
   (i) levothyroxine sodium in a concentration of 0.0025-5% by weight of the total formulation;
   (ii) arginine in a concentration of 0.0015-0.5% by weight of the total formulation;
   (iii) propylene glycol in a concentration of 0.002-0.05% by weight of the total formulation;
   (iv) sulfobutylether-β-cyclodextrin (SBECD) in a concentration of 10-40% by weight of the total formulation; and
   (v) one or more pharmaceutically acceptable excipients, wherein the pH of the formulation is between 5.5 and 6.5.

* * * * *

UNITED STATES PATENT AND TRADEMARK OFFICE
CERTIFICATE OF CORRECTION

| | | |
|---|---|---|
| PATENT NO. | : 11,364,196 B2 | |
| APPLICATION NO. | : 15/773619 | |
| DATED | : June 21, 2022 | |
| INVENTOR(S) | : Chandrashekhar et al. | |

It is certified that error appears in the above-identified patent and that said Letters Patent is hereby corrected as shown below:

On the Title Page

In the Assignee Item (73): Delete "LEIUTIS PHARMACEUTICALS PVT LTD" and insert
-- LEIUTIS PHARMACEUTICALS LLP --

Signed and Sealed this
Nineteenth Day of July, 2022

Katherine Kelly Vidal
*Director of the United States Patent and Trademark Office*